(12) United States Patent
Kwon et al.

(10) Patent No.: US 8,067,387 B2
(45) Date of Patent: Nov. 29, 2011

(54) METHOD FOR STIMULATING ANGIOGENESIS USING DKK2 AND COMPOSITION COMPRISING THE SAME

(75) Inventors: Young-Guen Kwon, Seoul (KR); Jeong-Ki Min, Gangwon-do (KR); Chae-Ok Yun, Seoul (KR); Young-Myeong Kim, Gangwon-do (KR)

(73) Assignee: Theragen Etex Co., Ltd, Siheung-Si (KR)

( * ) Notice: Subject to any disclaimer, the term of this patent is extended or adjusted under 35 U.S.C. 154(b) by 182 days.

(21) Appl. No.: 12/302,277

(22) PCT Filed: May 23, 2007

(86) PCT No.: PCT/KR2007/002493
§ 371 (c)(1), (2), (4) Date: Nov. 24, 2008

(87) PCT Pub. No.: WO2007/136226
PCT Pub. Date: Nov. 29, 2007

(65) Prior Publication Data
US 2009/0275509 A1    Nov. 5, 2009

(30) Foreign Application Priority Data

May 24, 2006  (KR) .................. 10-2006-0046442

(51) Int. Cl.
*A61K 48/00*  (2006.01)
*A61K 38/00*  (2006.01)
(52) U.S. Cl. ..................................... 514/44 R; 514/13.3
(58) Field of Classification Search .................. None
See application file for complete search history.

(56) References Cited

U.S. PATENT DOCUMENTS
2002/0172678 A1    11/2002    Ferrara et al.

FOREIGN PATENT DOCUMENTS
WO      WO 0012708 A      3/2000

*Primary Examiner* — Daniel C Gamett
(74) *Attorney, Agent, or Firm* — JHK Law; Joseph Hyosuk Kim (57) ABSTRACT

The present invention relates to a method for stimulating angiogenesis using by DKK2 and composition comprising the same. The DKK2 protein of the present invention showed stimulating activities of tube formation on HUVEC, promoting activity of the sprouting of arterial circle tissues and promoting activity of vascular development in the embryo of mouse. Therefore, it can be used as the therapeutics or functional health food for treating and preventing ischemic disease.

16 Claims, 8 Drawing Sheets

DKK2-transgenic mouse

Normal mouse

DKK2 transgenic mouse

[Fig. 11]

DA, descending aorta
SV, segmental vessel

SEQUENCE LISTING

<160> NUMBER OF SEQ ID NOS: 8

<210> SEQ ID NO 1
<211> LENGTH: 259
<212> TYPE: PRT
<213> ORGANISM: Artificial Sequence
<220> FEATURE:
<223> OTHER INFORMATION: Human amino acid sequence for DKK2

<400> SEQUENCE: 1

Met Ala Ala Leu Met Arg Ser Lys Asp Ser Ser Cys Cys Leu Leu Leu
1               5                   10                  15

Leu Ala Ala Val Leu Met Val Glu Ser Ser Gln Ile Gly Ser Ser Arg
            20                  25                  30

Ala Lys Leu Asn Ser Ile Lys Ser Ser Leu Gly Gly Glu Thr Pro Gly
        35                  40                  45

Gln Ala Ala Asn Arg Ser Ala Gly Met Tyr Gln Gly Leu Ala Phe Gly
    50                  55                  60

Gly Ser Lys Lys Gly Lys Asn Leu Gly Gln Ala Tyr Pro Cys Ser Ser
65                  70                  75                  80

Asp Lys Glu Cys Glu Val Gly Arg Tyr Cys His Ser Pro His Gln Gly
            85                  90                  95

Ser Ser Ala Cys Met Val Cys Arg Arg Lys Lys Lys Arg Cys His Arg

```
                    100                 105                 110
Asp Gly Met Cys Cys Pro Ser Thr Arg Cys Asn Asn Gly Ile Cys Ile
                115                 120                 125

Pro Val Thr Glu Ser Ile Leu Thr Pro His Ile Pro Ala Leu Asp Gly
            130                 135                 140

Thr Arg His Arg Asp Arg Asn His Gly His Tyr Ser Asn His Asp Leu
145                 150                 155                 160

Gly Trp Gln Asn Leu Gly Arg Pro His Thr Lys Met Ser His Ile Lys
                165                 170                 175

Gly His Glu Gly Asp Pro Cys Leu Arg Ser Ser Asp Cys Ile Glu Gly
            180                 185                 190

Phe Cys Cys Ala Arg His Phe Trp Thr Lys Ile Cys Lys Pro Val Leu
                195                 200                 205

His Gln Gly Glu Val Cys Thr Lys Gln Arg Lys Lys Gly Ser His Gly
            210                 215                 220

Leu Glu Ile Phe Gln Arg Cys Asp Cys Ala Lys Gly Leu Ser Cys Lys
225                 230                 235                 240

Val Trp Lys Asp Ala Thr Tyr Ser Ser Lys Ala Arg Leu His Val Cys
                245                 250                 255

Gln Lys Ile

<210> SEQ ID NO 2
<211> LENGTH: 780
<212> TYPE: DNA
<213> ORGANISM: Artificial Sequence
<220> FEATURE:
<223> OTHER INFORMATION: Human DNA sequence for DKK2

<400> SEQUENCE: 2
atggccgcgt tgatgcggag caaggattcg tcctgctgcc tgctcctact ggccgcggtg      60
ctgatggtgg agagctcaca gatcggcagt tcgcgggcca aactcaactc catcaagtcc     120
tctctgggcg gggagacgcc tggtcaggcc gccaatcgat ctgcgggcat gtaccaagga     180
ctggcattcg gcggcagtaa gaagggcaaa aacctgggcg aggcctaccc ttgtagcagt     240
gataaggagt gtgaagttgg gaggtattgc acagtcccc accaaggatc atcggcctgc     300
atggtgtgtc ggagaaaaaa gaagcgctgc caccgagatg gcatgtgctg ccccagtacc     360
cgctgcaata atggcatctg tatcccagtt actgaaagca tcttaacccc tcacatcccg     420
gctctggatg gtactcggca cagagatcga aaccacggtc attactcaaa ccatgacttg     480
ggatggcaga atctaggaag accacacact aagatgtcac atataaaagg gcatgaagga     540
gacccctgcc tacgatcatc agactgcatt gaagggtttt gctgtgctcg tcatttctgg     600
accaaaatct gcaaaccagt gctccatcag ggggaagtct gtaccaaaca acgcaagaag     660
ggttctcatg gctggaaat ttccagcgt tgcgactgtg cgaagggcct gtcttgcaaa     720
gtatggaaag atgccaccta ctcctccaaa gccagactcc atgtgtgtca gaaatttga     780

<210> SEQ ID NO 3
<211> LENGTH: 259
<212> TYPE: PRT
<213> ORGANISM: Artificial Sequence
<220> FEATURE:
<223> OTHER INFORMATION: mouse amino acid sequence for DKK2

<400> SEQUENCE: 3

Met Ala Ala Leu Met Arg Val Lys Asp Ser Ser Arg Cys Leu Leu Leu
1               5                   10                  15
```

-continued

| | | | | | | | | | | | |
|---|---|---|---|---|---|---|---|---|---|---|---|
|Leu|Ala|Ala|Val|Leu|Met|Val|Glu|Ser|Ser|Gln|Leu|Gly|Ser|Ser|Arg|
| | | |20| | | |25| | | |30|

Ala Lys Leu Asn Ser Ile Lys Ser Leu Gly Gly Glu Thr Pro Ala
          35                  40                  45

Gln Ser Ala Asn Arg Ser Ala Gly Met Asn Gln Gly Leu Ala Phe Gly
     50                  55                  60

Gly Ser Lys Lys Gly Lys Ser Leu Gly Gln Ala Tyr Pro Cys Ser Ser
65                  70                  75                  80

Asp Lys Glu Cys Glu Val Gly Arg Tyr Cys His Ser Pro His Gln Gly
             85                  90                  95

Ser Ser Ala Cys Met Leu Cys Arg Arg Lys Lys Arg Cys His Arg
             100                 105                 110

Asp Gly Met Cys Cys Pro Gly Thr Arg Cys Asn Asn Gly Ile Cys Ile
             115                 120                 125

Pro Val Thr Glu Ser Ile Leu Thr Pro His Ile Pro Ala Leu Asp Gly
         130                 135                 140

Thr Arg His Arg Asp Arg Asn His Gly His Tyr Ser Asn His Asp Leu
145                 150                 155                 160

Gly Trp Gln Asn Leu Gly Arg Pro His Ser Lys Met Pro His Ile Lys
                 165                 170                 175

Gly His Glu Gly Asp Pro Cys Leu Arg Ser Ser Asp Cys Ile Asp Gly
             180                 185                 190

Phe Cys Cys Ala Arg His Phe Trp Thr Lys Ile Cys Lys Pro Val Leu
         195                 200                 205

His Gln Gly Glu Val Cys Thr Lys Gln Arg Lys Lys Gly Ser His Gly
     210                 215                 220

Leu Glu Ile Phe Gln Arg Cys Asp Cys Ala Lys Gly Leu Ser Cys Lys
225                 230                 235                 240

Val Trp Lys Asp Ala Thr Tyr Ser Ser Lys Ala Arg Leu His Val Cys
                 245                 250                 255

Gln Lys Ile

<210> SEQ ID NO 4
<211> LENGTH: 780
<212> TYPE: DNA
<213> ORGANISM: Artificial Sequence
<220> FEATURE:
<223> OTHER INFORMATION: Human DNA sequence for DKK2

<400> SEQUENCE: 4
atggccgcgc tgatgcgggt caaggattca tcccgctgcc ttctcctact ggccgcggtg      60
ctgatggtgg agagctcaca gctaggcagc tcgcgggcca aactcaactc catcaagtcc     120
tctctaggag gggagactcc tgctcagtca gccaaccgat ctgcaggcat gaaccaagga     180
ctggctttcg gcggcagtaa aagggcaaa agcctggggc aggcctaccc ttgcagcagt     240
gataaggaat gtgaagttgg aagatactgc cacagtcccc accaaggatc atcagcctgc     300
atgctctgta ggaggaaaaa gaaacgatgc cacagagatg gatgtgttg ccctggtacc     360 cgctgcaata tggaatctg catcccagtc actgagagca tcctcacccc acatatccca     420
gctctggatg gcacccggca tagagatcgc aaccatggtc actattccaa ccatgacctg     480
ggatggcaga atctaggaag gccacactcc aagatgcctc atataaaagg acatgaagga     540
gacccatgcc tacggtcatc agactgcatt gatgggtttt gttgtgctcg ccacttctgg     600
accaaaatct gcaaaccagt gctccatcag ggggaagtct gtaccaaaca acgcaagaag     660
ggttcgcacg gctggagat tttccagagg tgtgactgtg caaagggcct gtcctgcaaa     720

```
gtgtggaaag atgccaccta ctcttccaaa gccagactcc atgtatgcca gaagatctga    780

<210> SEQ ID NO 5
<211> LENGTH: 21
<212> TYPE: DNA
<213> ORGANISM: Artificial Sequence
<220> FEATURE:
<223> OTHER INFORMATION: primer sequence of human DKK2

<400> SEQUENCE: 5
tagagattga gtttgagcct g                                              21

<210> SEQ ID NO 6
<211> LENGTH: 21
<212> TYPE: DNA
<213> ORGANISM: Artificial Sequence
<220> FEATURE:
<223> OTHER INFORMATION: reverse primer sequence of human DKK2

<400> SEQUENCE: 6
aaagggtgga cataagaaaa a                                              21

<210> SEQ ID NO 7
<211> LENGTH: 23
<212> TYPE: DNA
<213> ORGANISM: Artificial Sequence
<220> FEATURE:
<223> OTHER INFORMATION: primer sequence of mouse DKK2

<400> SEQUENCE: 7
ggcggcgtca ggaaggtagt atg                                            23

<210> SEQ ID NO 8
<211> LENGTH: 22
<212> TYPE: DNA
<213> ORGANISM: Artificial Sequence
<220> FEATURE:
<223> OTHER INFORMATION: reverse primer sequence of mouse DKK2

<400> SEQUENCE: 8
acactatgaa gccaggagtg gt                                             22
```

METHOD FOR STIMULATING ANGIOGENESIS USING DKK2 AND COMPOSITION COMPRISING THE SAME

TECHNICAL FIELD

The present invention relates to a method for stimulating angiogenesis using by DKK2 protein and the composition comprising the same.

BACKGROUND ART

Angiogenesis is a process by which new capillary blood vessels are formed. This process rarely occurs under normal biological condition but it always accompanied by embryogenesis, corpus luteum formation and wound healing. Particularly, angiogenesis plays an important role in tumor metastasis (Folkman J and Klagsburn M, *Science*, 235(4787), pp. 442-447, 1987).

Angiogenesis procedure consists of four steps, i.e., the $1^{st}$ step is the dissociation of capillary basal lamina by the action of protease enzyme caused by the stimulation of angiogenic factors, the $2^{nd}$ step is the migration and proliferation of blood endothelial cells, the $3^{rd}$ step is the formation of capillary tubes due to the differentiation of blood endothelial cell and the $4^{th}$ step is the reconstruction of new capillary blood vessels.

There have been reported that angiogenesis process is regulated by various stimulating factors and inhibiting factors, for example, growth factor, cytokine, lipid metabolism substance, cryptogenetic fragments of haemostatic protein etc (Folkman *J, Nat. Med.*, 1(1), pp. 27-31, 1995). Angiogenesis stimulating factors can be divided into several types, for example, mainly, cell growth inducing factor, cytokine having immune activity, hormone and lipid products etc (Bussolino F et al., *Trends. Biochem. Sci.*, 22(7), pp. 251-256, 1997).

However, the stimulating factors have various problems to be applied on clinical use since they act on not only vascular endothelial cell but also the other neighboring cells (Malecki M et al., *Gene Ther.*, Supple 1, pp. S159-169, 2005).

Accordingly, recent research has been focused on founding important gene acting only on blood endothelial cell, in particular, being involved in angiogenesis and new method for treating various disease requiring angiogenesis using by the gene. However, there have not been achieved satisfactory results till now.

Therapeutic angiogenesis is a method for treating ischemic disease by promoting the formation of collateral vessels through administering the angiogenic factors such as vascular endothelial growth factor (VEGF), fibroblast growth factor (FGF), developmentally regulated endothelial locus-1 (Del-1), hepatocyte growth factor (HGF), platelet-derived endothelial cell growth factor (PD-EGF), angiopoietin, transforming growth factor (TGF) and epidermal growth factor (EGF) etc or the gene encoding the same, and it has been highlighted as a new method for treating severe ischemic disease which could not been performed to percutaneous transluminal coronary angioplasty (PTCA) and coronary artery bypass grafting (CABG) method (Kim D. K. and Kwon H. C., *The journal of endocrinology*, 16(3), pp. 328-338, 2001).

DKK2, a repressor protein of Wnt protein, has been reported to act as an inhibiting factor or stimulating factor of signaling pathways of Wnt (Wu W et al., *Curr. Biol.*, 10(24), pp. 1611-1614, 2000). It has two specific cysteine-rich domains and is divided into various lengths of connection regions. Particularly, the protein belonged to Dickkopf family highly conserves cystein-2 region between the family members as well as 10 cysteines (Krupnik V E et al., *Gene*, 238(2), pp. 301-313, 1999). It has been reported that DKK2 is closely correlated with the differentiation of osteoclast (Li X et al., *Nat. Genet.*, 37(9), pp. 945-952, 2005).

However, there has been not reported or disclosed about the effect on stimulating activity of DKK2 on angiogenesis in any of above cited literatures, the disclosures of which are incorporated herein by reference.

DISCLOSURE OF INVENTION

Technical Problem

Accordingly, the present inventors of the present invention have intensively studied to find several differentiation-control genes in endothelial cell and new effective method for stimulating angiogenesis, finally, they have found that DKK2 shows potent stimulating effect on angiogenesis and thus the protein could be useful in treatment and prevention of ischemic diseases.

Technical Solution

In accordance with the present invention, the present invention provides a method for stimulating angiogenesis in a mammal, comprising the step of administering to the vascular-unformed tissue of the mammal an effective amount of DKK2 protein or DKK2 protein-encoding DNA.

The term "vascular-unformed tissue of the mammal" disclosed herein comprises newly formed dermal tissue, muscular tissue and connective tissue after the injuring caused by ischemic disease in mammal.

The term "ischemic disease" disclosed herein comprises burn, psoriasis, ulcer, ischemia, myocardial infarction, angina pectoris, cerebral infarction or cerebral hemorrhage.

The term "DKK2 protein-encoding DNA" disclosed herein is administered to mammal using by viral vectors or non-viral vectors.

The term "non-viral vectors" disclosed herein comprises the plasmid which can be expressed in animal cells.

The term "viral vectors" disclosed herein comprises adenovirus vector, adeno-associated virus vector, retrovirus vector, lentivirus vector or herpes simplex virus vector.

It is another object of the present invention to provide a pharmaceutical composition comprising DKK2 protein or DKK2 protein-encoding DNA as an active ingredient in an effective amount to treat and prevent ischemic disease.

It is the other object of the present invention to provide a use of DKK2 protein or DKK2 protein-encoding DNA for the manufacture of medicines employed for treating or preventing ischemic disease.

It is the other object of the present invention to provide a method for treating or preventing ischemic disease, wherein said method comprises administering a therapeutically effective amount of DKK2 protein or DKK2 protein-encoding DNA into the mammal suffering with the diseases caused by angiogenesis.

Also, it is another object of the present invention to provide a health care food composition comprising DKK2 protein or DKK2 protein-encoding DNA as an active ingredient in an effective amount to prevent and alleviate ischemic disease.

The term "DKK2 protein" disclosed herein comprises the amino acid represented by SEQ ID NO: 1.

The term "DKK2 protein-encoding DNA" disclosed herein comprises the gene represented by SEQ ID NO: 2.

Above described DKK2 sequences is not limited to the DKK2 sequences of mammal but comprise all the DKK2 in mammals.

Above described DKK2 protein comprises DKK2 protein isolated from the tissues of mammal or recombinant DKK2 proteins.

The inventive DKK2 protein or DKK2 protein-encoding DNA may be prepared in accordance with the following preferred embodiment.

Hereinafter, the present invention is described in detail.

For the present invention, the above-described DKK2 protein and gene encoding the same can be prepared by following procedure. The entire RNA purified from HUVEC is performed to reverse transcription to obtain complimentary DNA; PCR is performed with the obtained complimentary DNA as a template and DKK2 primers, preferably, the DKK2 primers represented by SEQ ID NO: 5 and SEQ ID NO: 6 to obtain amplified DKK2 genes.

The above-described DKK2 proteins can be obtained by following process, for example, the DKK2 genes prepared by the above described step are treated with restriction enzyme, cloned into plasmid to obtain the plasmid, which may be cloned and transformed with expression cell lines; the transformed cells are selected and the secreted DKK2 proteins in the medium are purified with column; or DKK2 genes prepared by the above described step are introduced into vector, preferably lentivirus vector, cultured in medium, and the secreted DKK2 proteins in the medium are purified with column.

DKK2-introduced cell lines and the DKK2 gene prepared by the above described step shows stimulating activities of tube formation on HUVEC, promoting activity of sprouting on arterial circle tissues and promoting activity of vascular development of embryo in mouse. Additionally, not only full-length of the DKK2 but also fragments of the DKK2 show similar stimulating activity of angiogenesis each other.

It is another object of the present invention to provide a pharmaceutical composition comprising DKK2 protein or DKK2 protein-encoding DNA prepared from the above-described method as an active ingredient in an effective amount to treat and prevent ischemic disease.

It is the other object of the present invention to provide a use of a DKK2 protein or DKK2 protein-encoding DNA prepared from the above-described method for manufacture of medicines employed for treating or preventing ischemic disease.

It is the other object of the present invention to provide a method for treating or preventing ischemic disease, wherein said method comprises administering a therapeutically effective amount of a DKK2 protein or DKK2 protein-encoding DNA prepared from the above-described method into the mammal suffering with ischemic disease.

The inventive composition for treating ischemic disease may comprise the above described DKK2 protein or the DNA encoding the same as 0.1-50% by weight based on the total weight of the composition.

The inventive composition may additionally comprise conventional carrier, adjuvants or diluents in accordance with a using method well known in the art. It is preferable that said carrier is used as appropriate substance according to the usage and application method, but it is not limited. Appropriate diluents are listed in the written text of Remington's Pharmaceutical Science (Mack Publishing co, Easton Pa.).

Hereinafter, the following formulation methods and excipients are merely exemplary and in no way limit the invention.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents that are commonly used to produce an injection. Suitable examples of the carriers include physiological saline, polyethylene glycol, ethanol, vegetable oils, isopropyl myristate, etc., but are not limited to them. For topical administration, the composition of the present invention can be formulated in the form of ointments and creams.

Pharmaceutical formulations containing present composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

For example, the compositions of the present invention can be dissolved in oils, propylene glycol or other solvents that are commonly used to produce an injection. Suitable examples of the base or carrier in the injection include various salt mixture such as physiological saline, inorganic salt or the mixture thereof; sugar solution such as mannitol, lactose, dextran etc; amino acid such as glycine, arginine etc; polyethylene glycol, ethanol, vegetable oils, isopropyl myristate, organic acid solution, salt solution, or the mixture thereof etc, but are not limited to them. The injectable preparation of the present invention may be prepared by adding conventional additives in injection, for example, osmotic controller, pH controller, vegetable oil, lecithin, surfactant such as non-ionic surfactant to the above-described base in order to make appropriate formulation such as solution, suspension, colloidal solution etc. In case of solid composition of the present invention, the composition is dissolved in sterilized base prior to use in situ in genetic therapy and liquid composition of the present invention may be used directly without particular treatment.

For topical administration, the composition of the present invention can be formulated in the form of ointments and creams.

The composition of the present invention in pharmaceutical dosage forms may be used in the form of their pharmaceutically acceptable salts, and also may be used alone or in appropriate association, as well as in combination with other pharmaceutically active ingredients.

The DKK2 protein-encoding DNA disclosed herein to be supplied into the affected part may be used in the inserted form of vectors, for example adenovirus vector, adeno-associated virus vector, retrovirus vector, lentivirus vector, herpes simplex virus vector or plasmid expressed in mammal cells.

The desirable dose of the inventive composition varies depending on the condition and the weight of the subject, severity, drug form, route and period of administration, and may be chosen by those skilled in the art. However, in order to obtain desirable effects, it is generally recommended to administer at the amount ranging from 0.001 to 100 mg/kg, preferably, 0.1 to 100 mg/kg by weight/day of the inventive protein or DNA of the present invention. The dose may be administered in single or divided into several times per day.

It is still another object of the present invention to provide a health care food comprising DKK2 protein or DKK2 protein-encoding DNA as an active ingredient for preventing and improving ischemic disease.

The above-described composition therein can be added to food, additive or beverage, wherein, the amount of the above described protein or DNA in food or beverage may generally range from about 0.01 to 95 w %, preferably 1 to 80 w % of total weight of food for the health care food composition.

The present invention provides a composition of the health care beverage comprising DKK2 protein or DKK2 protein-encoding DNA for preventing and alleviating ischemic disease in mammal.

To develop for health care food, examples of addable food comprising the above-described DKK2 protein or DKK2 protein-encoding DNA of the present invention are various food, beverage, gum, vitamin complex, health improving food and the like, and can be used as powder, granule, tablet, chewing tablet, capsule or beverage etc.

Inventive composition of the present invention has no toxicity and adverse effect therefore they can be used with safe.

The above-described composition therein can be added to food, additive or beverage, wherein, the amount of the above-described DKK2 protein or DKK2 protein-encoding DNA in food or beverage may generally range from about 0.01 to 80 w/w %, preferably 0.01 to 15 w/w % of total weight of food for the health food composition and 0.02 to 5 g, preferably 0.3 to 1 g on the ratio of 100 ml of the health care beverage composition.

Providing that the health care beverage composition of present invention contains the above-described DKK2 protein or DKK2 protein-encoding DNA as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition. Examples of addable food comprising aforementioned extract therein are various food, beverage, gum, vitamin complex, health improving food and the like.

The inventive composition may additionally comprise one or more than one of organic acid, such as citric acid, fumaric acid, adipic acid, lactic acid, malic acid; phosphate, such as phosphate, sodium phosphate, potassium phosphate, acid pyrophosphate, polyphosphate; natural anti-oxidants, such as polyphenol, catechin, α-tocopherol, rosemary extract, vitamin C, green tea extract, licorice root extract, chitosan, tannic acid, phytic acid etc.

The above-described inventive DKK2 protein or DKK2 protein-encoding DNA may be 20 to 90% high concentrated liquid, power, or granule type.

Similarly, the above-described DKK2 protein or DKK2 protein-encoding DNA can comprise additionally one or more than one of lactose, casein, dextrose, glucose, sucrose and sorbitol.

Inventive DKK2 protein or DKK2 protein-encoding DNA of the present invention has no toxicity and adverse effect therefore; they can be used with safe.

It will be apparent to those skilled in the art that various modifications and variations can be made in the compositions, use and preparations of the present invention without departing from the spirit or scope of the invention.

Advantageous Effects

As described in the present invention, the DKK2 protein or DKK2 protein-encoding DNA showed stimulating activities of tube formation on HUVEC, promoting activity of the sprouting of arterial circle tissues and promoting activity of vascular development in the embryo of mouse. Therefore, it can be used as the therapeutics or functional health food for treating and preventing ischemic disease.

BRIEF DESCRIPTION OF THE DRAWINGS

The above and other objects, features and other advantages of the present invention will more clearly understood from the following detailed description taken in conjunction with the accompanying drawings, in which.

BEST MODE FOR CARRYING OUT THE INVENTION

It will be apparent to those skilled in the art that various modifications and variations can be made in the compositions, use and preparations of the present invention without departing from the spirit or scope of the invention.

The present invention in more specifically explained by the following examples. However, it should be understood that the present invention is not limited to these examples.

Mode for the Invention

The following Reference Example and Experimental Examples are intended to further illustrate the present invention without limiting its scope.

Reference Example 1

Cultivation of HUVEC

HUVECs (Human umbilical vein endothelial cell) were isolated from the umbilical cords obtained from gynecology department of Yonsei University Hospital according to following process. After washing veins with Cord buffer (0.2% glucose phosphate buffered saline), 5 ml of 0.2% type I collagenase (Sigma-Aldrich Co., Mo., USA) was added to the veins and the veins were left alone at 37° C. for 5 min. After adding 20 ml of cord buffer to veins at room temperature, the vein cells separated from the opposite end were collected. The cord buffer was added to the veins again to react at 37° C. The collected human umbilical vein endothelial cells (HUVECs) was washed and poured to the coated T75 flask used for tissue culture with 0.1% of gelatin. The cells were cultured in EGM™-2 complete medium (Cambrex, Md., USA) in 5% $CO_2$ culture incubator at 37° C. and when the cells became to confluent phase, the cells were separated from trypsin-EDTA solution. The cells of 3-4 passage obtained from the above process were used in the experiment.

Reference Example 2

Preparation of DKK2 Regulated Cell Lines Using Lentivirus Vector

The DKK2-recombinated viruses obtained from the over-expressed and repressed cell lines of DKK2 prepared by transforming cloned plasmid to virus production cell lines using by lentivirus, were purchased from Macrogen Inc (South Korea). 48 hours after the addition of DKK2 virus to HUVECs prepared in Reference Example 1, the isolated RNA from the cells was performed to reverse-transcription and polymerization to confirm the expression level of DKK2 mRNA as follows: total RNA was isolated using by TRIzol reagent (Invitrogen, USA), performed to reverse transcription using by oligo (dT) primer and following PCR cycles were repeated 30 times using by reverse transcriptase (Stratagen, USA); pre-denaturation at 94° C. for 5 min using by polymerase (Stratagen, USA), denaturation at 94° C. for 30 sec, annealing at 50° C. for 30 sec using by primers and extension at 72° C. for 30 sec.

Figure 3:
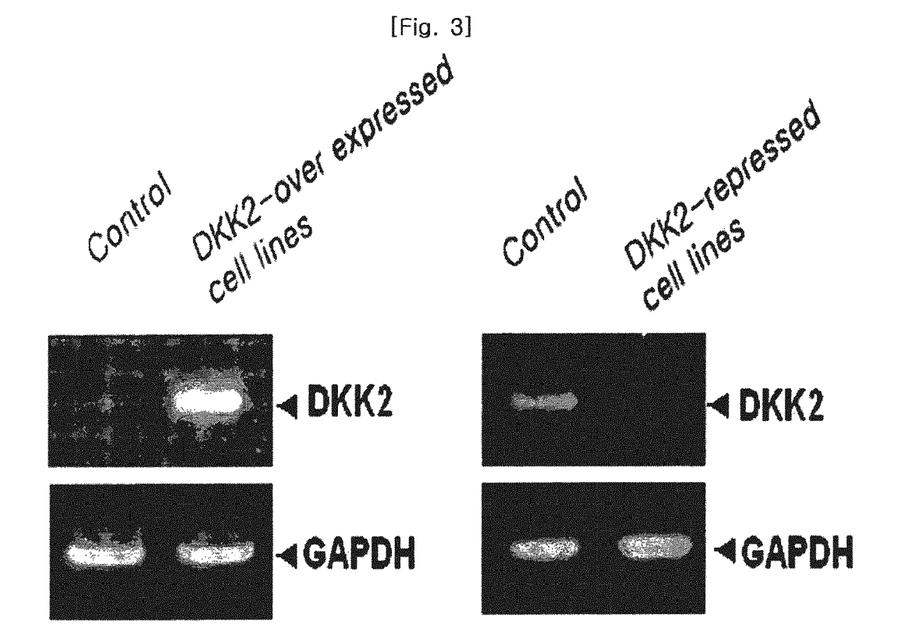
FIG. 3 represents the production result of DKK2 expression cell line and DKK2 repression cell line using by lentiviruses.

As shown in FIG. 3, the results demonstrate that the over expression cell lines and repression cell lines of DKK2 were well-produced.

Reference Example 3

Preparation of DKK2-transgenic Mouse

Figure 6:
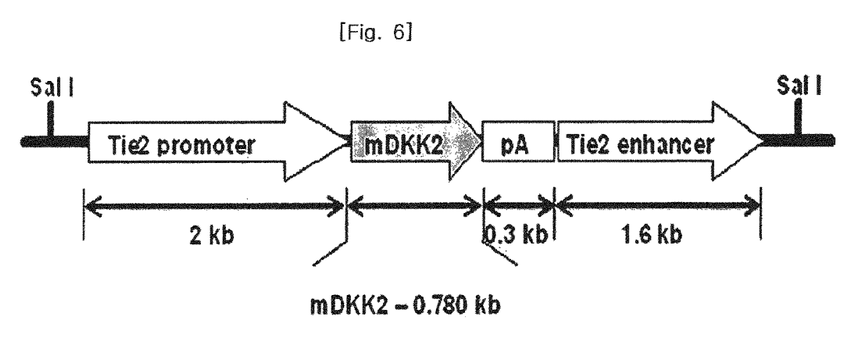
FIG. 6 presents the vector diagram for the production of DKK2-transgenic mouse.
Figure 7:
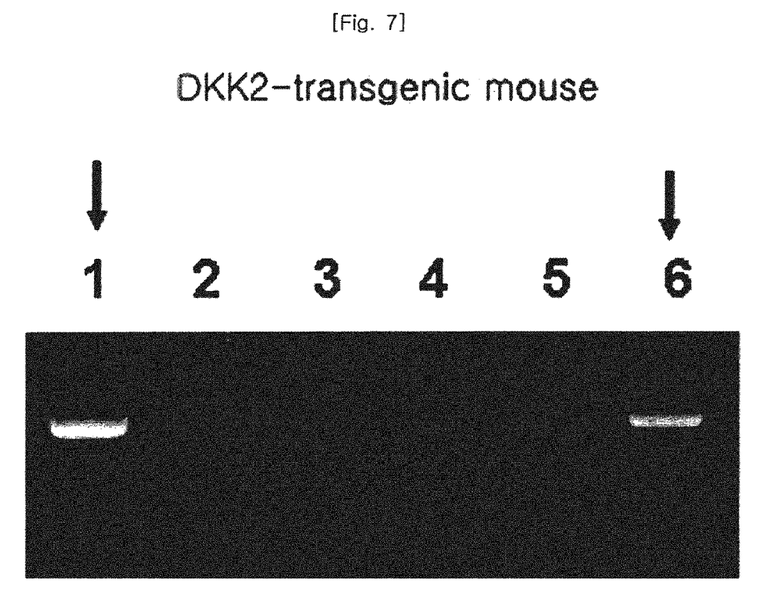
FIG. 7 represents the confirmation of DKK2-transgenic mouse by DNA amplification.

The DKK2 over-expression mouse was prepared using the Tie2 transcription regulatory region activated in only vascular endothelial cells to determine the effect of DKK2 gene on angiogenesis in vivo (Schlaeger T M et al., *Proc. Natl. Acad. Sci*. USA, 94(7, pp. 3058-3063, 1997). As shown in FIG. 6, mouse DKK2 gene represented by SEQ ID NO: 4 was treated with HindIII and NotI(NEB, England) and cloned into Psp vector (Clontech, USA). The cloned plasmid was treated with SalI(NEB, England) to prepare DNA fragments and the prepared DNA fragments were injected into the ovules isolated from the mouse (C57BL6, Orient Inc, Korea) of which ovulation had been stimulated by gonadotropin releasing-hormone (Sigma, USA) to induce transduction, and then, the DKK2-transgenic ovules were implanted on surrogate mother mouse after fertilization. The tail of the mouse born after the $21^{st}$ fertilization was cut, treated with proteinase K (Sigma, USA) to isolate DNA, and the isolated DNA was amplified by PCR [(pre-denaturation at 94° C. for 5 min, denaturation at 94° C. for 30 sec, annealing at 55° C. for 30 sec and extension at 72° C. for 30 sec)×30 cycles and post-extension at 72° C. for 10 min] using the DKK2 primers represented by SEQ ID NO: 7 and SEQ ID NO: 8. (See FIG. 7).

Experimental Example 1

DKK2 Expression Spectra During the Differentiation of Human Umbilical Vein Endothelial Cells 250 µl of Matrigel (Collaborative Biomedical Products, USA; density: 10 mg proteins ml) was added to the well plates with the diameter of 16 mm and performed to polymerization at 37° C. for 30 min. The HUVECs prepared in Reference Example 1 were cultured in M199 growth medium (Invitrogen, USA) containing 20% (v/v) fetal bovine serum (FBS, Hyclone, USA), 100 units/ml of penicillin (Invitrogen, USA), 10 µg/ml of streptomycin (Invitrogen, USA), 3 ng/ml of bFGF (basic fibroblast growth factor; Upstate Biotechnology, USA) and 5 units/ml of heparin (Sigma, USA) and trypsin was added thereto to obtain cultured cells. The cells were suspended in the growth medium and spread onto Matrigel layer in the concentration of $2 \times 10^5$ cells/well to induce the differentiation of cells (See FIG. 1).

Figure 1:
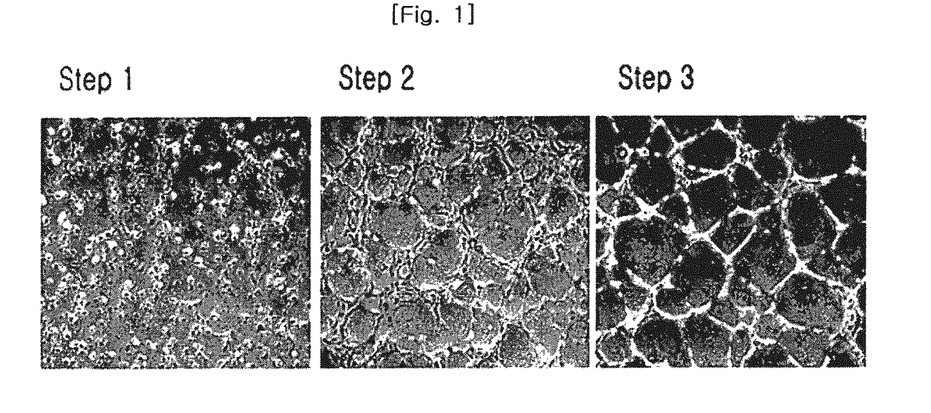
FIG. 1 shows the differentiation feature of the HUVEC (Human umbilical vein endothelial cell) on Matrigel.

As shown in FIG. 1, differentiation consists of 3 steps; the $1^{st}$ step is the beginning of differentiation used as control group, the $2^{nd}$ step is the formation of blood vessel-like structure due to cell transfer and the $3^{rd}$ step is the completion of blood vessel-like structure formation.

Figure 2:
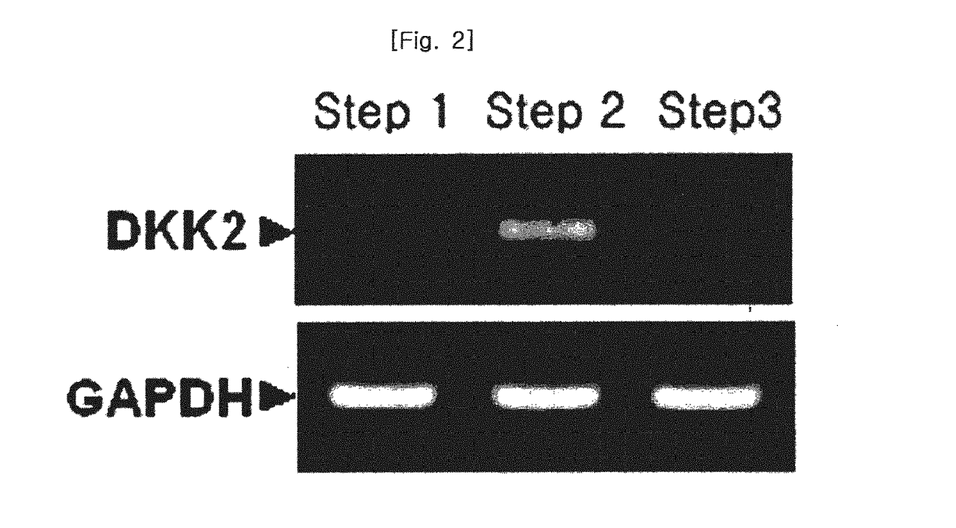
FIG. 2 represents the expression of DKK2 gene on differentiation of the HUVEC.

After isolating RNA from the cells in each step using by TRIZOL solution (Invitrogen, USA), the isolated RNA was performed to reverse transcription using the primers represented by SEQ ID NO: 5 and SEQ ID NO:6, and amplification according to the process disclosed in Reference Example 3 (See FIG. 2).

As shown in FIG. 2, the results demonstrate that the expression of DKK2 genes was increased during the tube formation. It has been confirmed that the DKK2 is positive regulator of tube formation.

Experimental Example 2

The Effect of DKK2 on Tube Formation of Human Umbilical Vein Endothelial Cells

250 µl of Matrigel (Collaborative Biomedical Products, USA; density: 10 mg proteins/ml) was added to the well plates with the diameter of 16 mm and performed to polymerization at 37° C. for 30 min, The HUVECs prepared in Reference Example 2 were cultured in M199 growth medium (Invitrogen, USA) containing 20% (v/v) fetal bovine serum (FBS, Hyclone, USA), 100 units/ml of penicillin (Invitrogen, USA), 10 μg/ml of streptomycin (Invitrogen, USA), 3 ng/ml of bFGF (basic fibroblast growth factor; Upstate Biotechnology, USA) and 5 units/ml of heparin (Sigma, USA) and trypsin was added thereto to obtain cultured cells. The cells were suspended in the growth medium and spread onto Matrigel layer in the concentration of $2\times10^5$ cells/well to induce the differentiation of cells (See FIG. 4). The cells were cultured for 20 hours. The rate of tube formation was measured by an optical microscopy (ZEISS, Germany).

Figure 4:
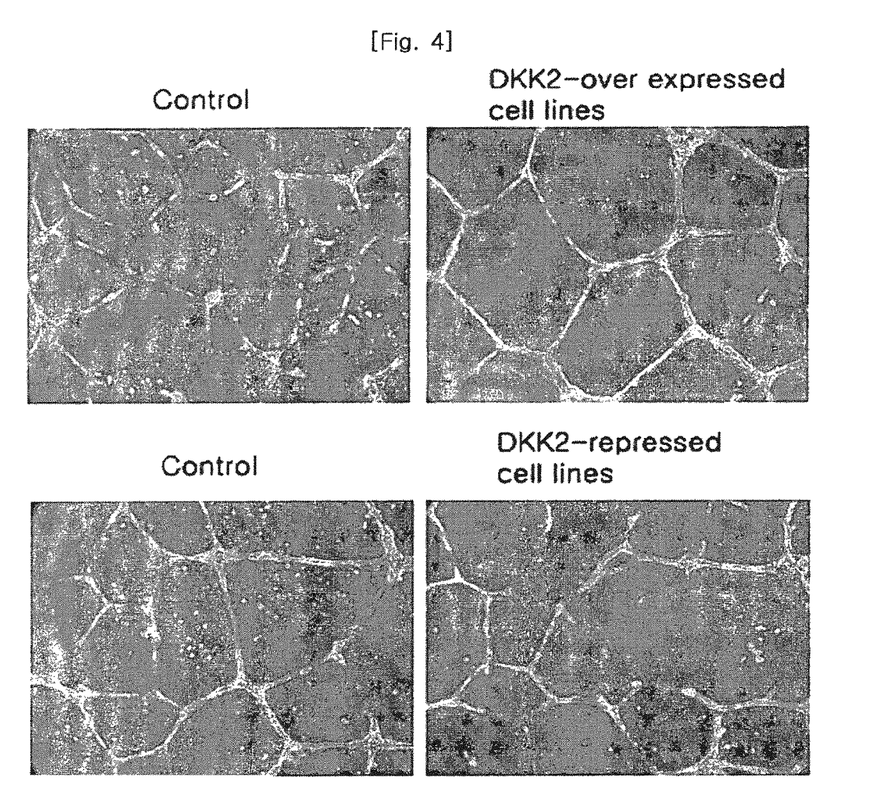
FIG. 4 shows the comparison result of tube formation on DKK2 expression and repression cell lines.

As shown in FIG. 4, the results demonstrate that the tube formation was induced on expression cell line of DKK2, but decreased on repression cell line of DKK2.

Experimental Example 3

The Stabilization Effect of DKK2 on β-catenin

The over-expression cell lines of DKK2 using by lentivirus system prepared in Reference Example 2 were cultured for 24 hrs. The medium was replaced into M199 growth medium containing 20% (v/v) of fetal bovine serum (FBS, Hyclone, USA), 100 units/ml of penicillin (Invitrogen, USA), 10 μg/ml of streptomycin (Invitrogen, USA), 3 ng/ml of bFGF (basic fibroblast growth factor; Upstate Biotechnology, USA) and 5 units/ml of heparin (Sigma, USA), and 200 ng/ml sFrizzle (BD bioscience, USA) was added thereto as a Wnt secretion inhibitor. After culturing for 24 hrs, trypsin was treated thereto to obtain the cultured cells. DNA was separated from the cells using by lysis buffer containing 100 mM of Tris/Cl, 5 mM of EDTA, 50 mM of beta-glycerophosphate, 50 mM of NaF, 100 μM of $Na_3VO_4$, 1 mM of PMSF, 0.5% of NP-40 and 1% of Triton X-100. The expression level of the separated DNA was confirmed through the western blot test using by the antibody of β-catenin (Upstate Biotechnology, USA).

Figure 5:
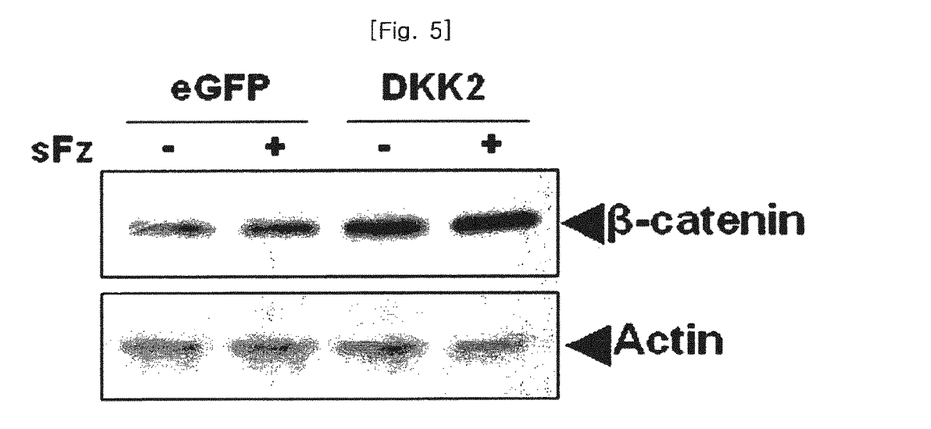
FIG. 5 represents the increasing result of β-catenin protein by the treatment of DKK2 distinct from Wnt signal.

As shown in FIG. 5, the expression level of β-catenin protein was significantly increased by DKK2 compared with control group (eGFP), and the increased level was not reduced in spite of the treatment of Wnt repressor (sFz). Accordingly, it has been confirmed that DKK2 stimulates the angiogenesis by controlling the expression level of β-catenin protein as distinct from Wnt signal.

Experimental Example 4

The Effect of DKK2 on the Sprouting of Endothelial Cells From Aorta of DKK2-transgenic Mouse The aorta which had been isolated from the back region of DKK2-transgenic mouse prepared in Reference Example 3 and 6-weeks-old normal mouse were cut into the size of 1 mm and the arterial circle tissues were laid on 48-well plates coated with 110 μl of matrigel. The well was sealed again with 40 μl of Matrigel and HUVEC culture medium (SFM, Invitrogen, USA) was added to each well to the extent the final volume of each well reached to 200 μl. After 5 days, the number of sprout formed from each circle was counted and the rate of sprout in DKK2-transgenic mouse group was compared with that in control mouse group (See FIG. 8). The rate of sprout was scored by dividing the sprout into five parts according to following criteria; 5 points was assigned in case that all the 5 parts were sprouted, 0 points was assigned in case that none was sprouted.

Figure 8:
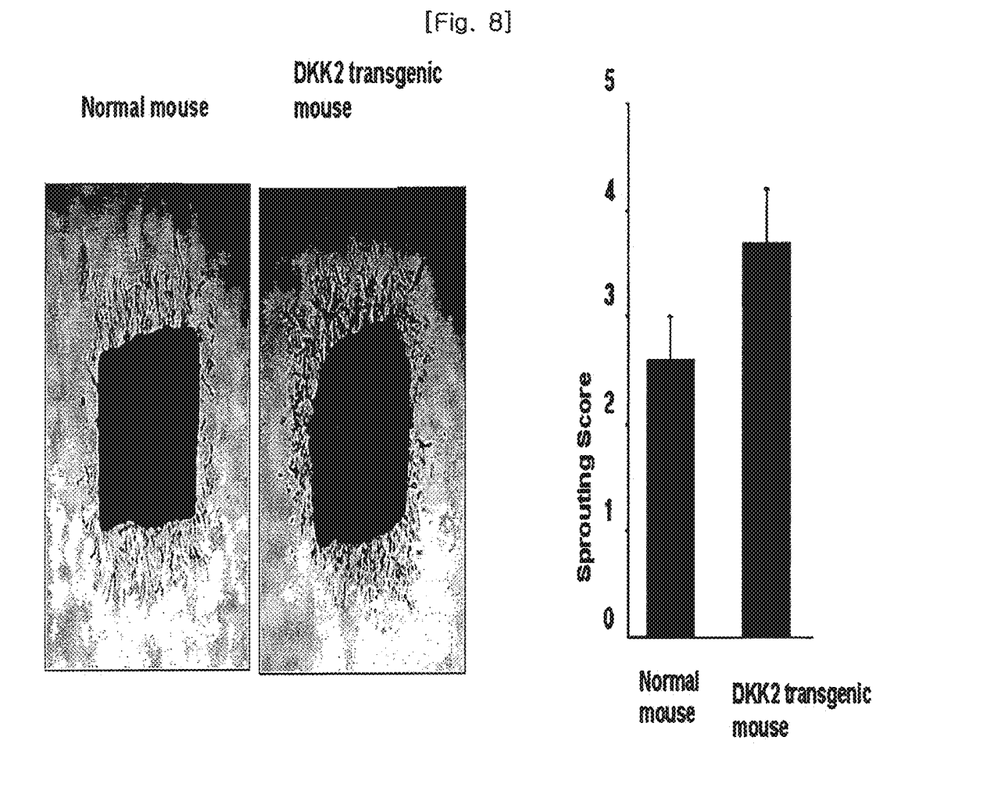
FIG. 8 presents the induction of the sprouting of endothelial cells from aorta of DKK2-transgenic mouse

As can be seen in FIG. 8, the result demonstrates that the sprouting of the arterial circle tissues in DKK2-transgenic mouse was significantly increased compared with that in normal mouse.

Experimental Example 5

The Effect of DKK2 on the Development of Blood Vessel in the Embryo of DKK2-transgenic Mouse The embryos delivered from the $9^{th}$ to $10^{th}$ day pregnant normal and DKK2-transgenic mice were fixed with 4% paraformaldehyde for a day and stained with the antibody of von Willebrand Factor (WF) (Chemicon, USA) specifically expressed only on vascular endothelial cells to observe the development of blood vessel by the method disclosed in literature (Sadler J. E., *J. Thromb. Haemost.*, 3(8), pp 1702-1709, 2005).

Figure 9:
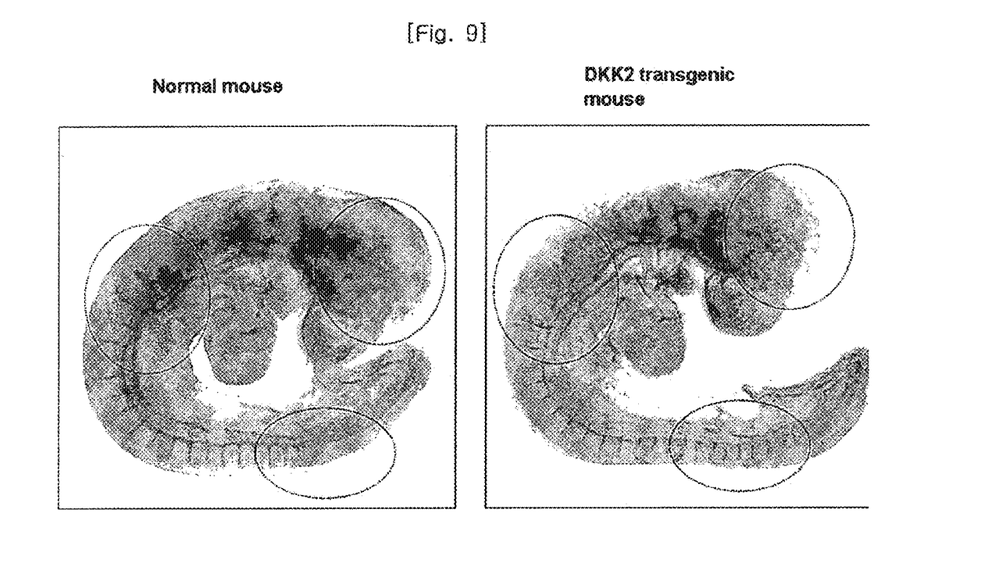
FIG. 9 shows the vessel development on embryo of normal mouse and DKK2-transgenic mouse using the antibody of vWF which is vessel-specific protein.

As can be seen in FIG. 9, the results demonstrate that angiogenesis and vascular development are generally increased in the embryo of DKK2-transgenic mouse compared with the normal mouse control.

Figure 10:
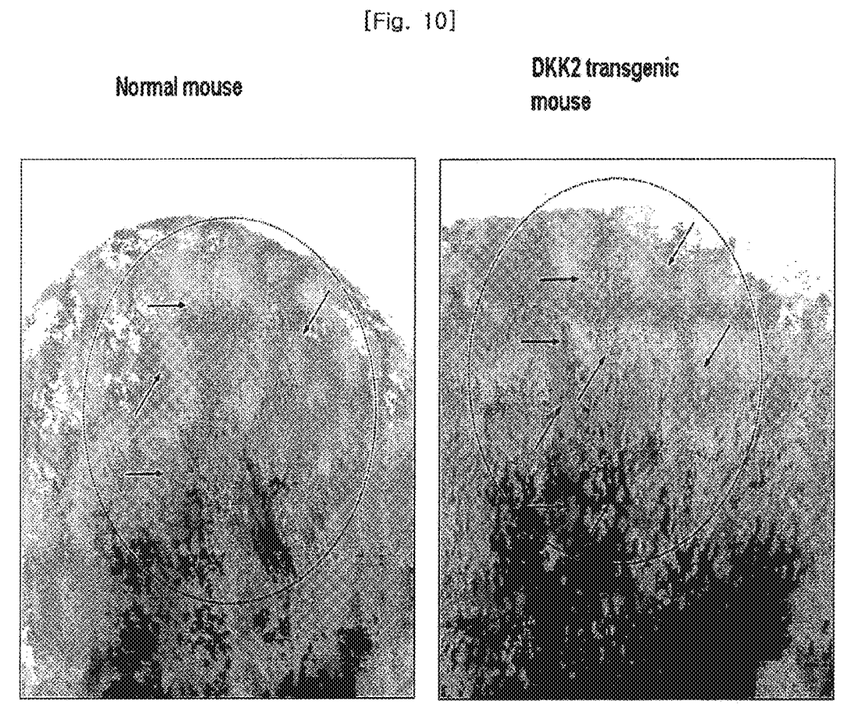
FIG. 10 shows the comparison results of angiogenesis on the head region of embryo of normal mouse and DKK2-transgenic mouse.
Figure 11:
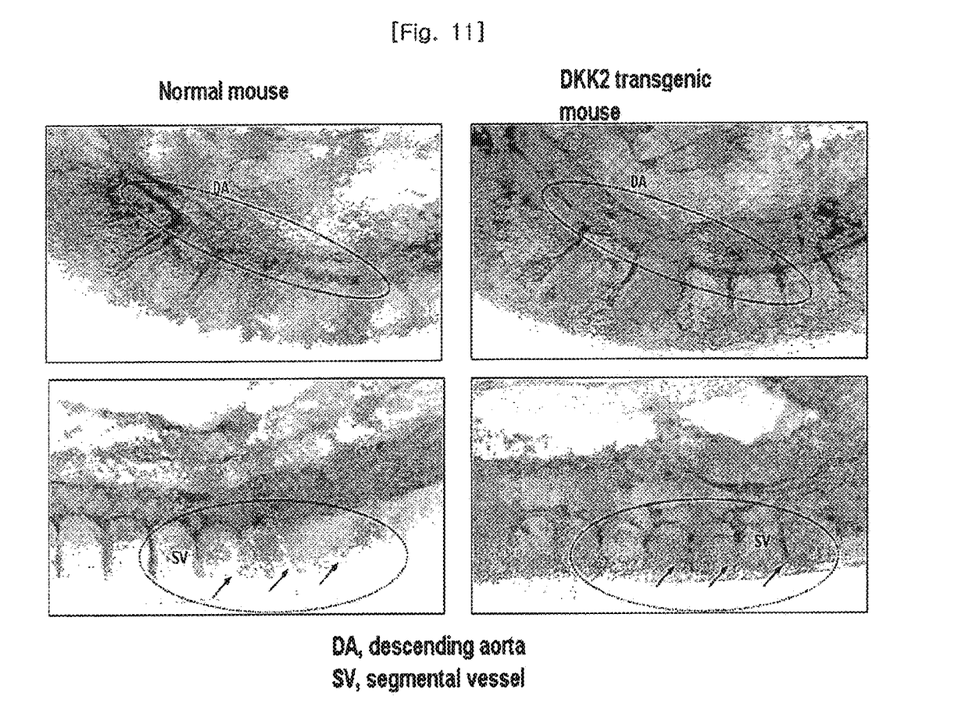
FIG. 11 presents the growth of descending aorta and segmental vessel on the embryo of normal mouse and DKK2-transgenic mouse.

To verify the effect of DKK2 on the angiogenesis of embryo, the development of head capillary plexus, descending aorta and segmental vessels in the embryos prepared by the above-described process was determined by high magnification.

As shown in FIGS. 10 and 11, the results demonstrate that the significantly enhanced growth of head capillary plexus and segmental vessel and enlarged descending aorta on embryos of DKK2-transgenic mouse was promoted.

Hereinafter, the formulating methods and kinds of excipients will be described, but the present invention is not limited to them. The representative preparation examples were described as follows.

Preparation of Injection
DKK2 protein 100 mg
Sodium metabisulfite 3.0 mg
Methyl paraben 0.8 mg
Propyl paraben 0.1 mg
Distilled water for injection optimum amount Injection preparation was prepared by dissolving active component, controlling pH to about 7.5 and then filling all the components in 2 ml ampules and sterilizing by conventional injection preparation method.

Preparation of Powder
DKK2 protein 500 mg
Corn Starch 100 mg
Lactose 100 mg
Talc 10 mg Powder preparation was prepared by mixing above components and filling sealed package.

Preparation of Tablet
DKK2 protein 200 mg
Corn Starch 100 mg
Lactose 100 mg
Magnesium stearate optimum amount Tablet preparation was prepared by mixing above components and entabletting.

Preparation of Capsule
DKK2 protein 100 mg
Lactose 50 mg
Corn starch 50 mg
Talc 2 mg
Magnesium stearate optimum amount Tablet preparation was prepared by mixing above components and filling gelatin capsule by conventional gelatin preparation method.

Preparation of Liquid
DKK2 protein 1000 mg
Sugar 20 g
Polysaccharide 20 g
Lemon flavor 20 g Liquid preparation was prepared by dissolving active component, and then filling all the components in 1000 ml ampules and sterilizing by conventional liquid preparation method.

Preparation of Health Food
DKK2 protein 1000 mg
Vitamin mixture optimum amount
Vitamin A acetate 70 mg
Vitamin E 1.0 mg
Vitamin $B_1$ 0.13 mg
Vitamin $B_2$ 0.15 mg
Vitamin B 60.5 mg
Vitamin B 120.2 mg
Vitamin C 10 mg
Biotin 10 mg
Amide nicotinic acid 1.7 mg
Folic acid 50 mg
Calcium pantothenic acid 0.5 mg
Mineral mixture optimum amount
Ferrous sulfate 1.75 mg
Zinc oxide 0.82 mg
Magnesium carbonate 25.3 mg
Monopotassium phosphate 15 mg
Dicalcium phosphate 55 mg
Potassium citrate 90 mg
Calcium carbonate 100 mg
Magnesium chloride 24.8 mg The above mentioned vitamin and mineral mixture may be varied in many ways. Such variations are not to be regarded as a departure from the spirit and scope of the present invention.

Preparation of Health Beverage
DKK2 protein 1000 mg
Citric acid 1000 mg
Oligosaccharide 100 g
Apricot concentration 2 g
Taurine 1 g
Distilled water 900 ml Health beverage preparation was prepared by dissolving active component, mixing, stirred at 85° C. for 1 hour, filtered and then filling all the components in 1000 ml ampules and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the DKK2 showed stimulating activities of tube formation on HUVEC, promoting activity of the sprouting of arterial circle tissues and promoting activity of vascular development in the embryo of mouse. Therefore, it can be used as the therapeutics or functional health food for treating and preventing ischemic disease.

Sequence Listing

SEQ ID NO: 1 is amino acid sequence of human DKK2, SEQ ID NO:2 is DNA sequence of human DKK2, SEQ ID NO:3 is amino acid sequence of mouse DKK2, SEQ ID NO:4 is DNA sequence of mouse DKK2, SEQ ID NO:5 is forward primer sequence of human DKK2, SEQ ID NO:6 is reverse primer sequence of human DKK2, SEQ ID NO:7 is forward primer sequence of mouse DKK2, and SEQ ID NO:8 is reverse primer sequence of mouse DKK2.

---

The invention claimed is:

1. A method for stimulating angiogenesis in a mammal, comprising administering to the mammal an effective amount of lentivirus vector containing DKK2 protein-encoding DNA to newly forming tissue at a site of tissue damage.

2. The method according to claim 1, wherein said DKK2 protein comprises the amino acid sequence represented by SEQ ID NO: 1.

3. The method according to claim 1, wherein said DNA protein comprises the nucleic acid sequence represented by SEQ ID NO: 2.

4. The method according to claim 1, wherein the mammal is a human being.

5. The method according to claim 1, wherein the tissue damage is caused by ischemic disease.

6. The method according to claim 5, wherein said ischemic disease is a burn, an ulcer, a myocardial infarction, an angina pectoris, a cerebral infarction, or a cerebral hemorrhage.

7. The method according to claim 6, wherein the ischemic disease is a burn.

8. The method according to claim 6, wherein the ischemic disease is ulcer.

9. The method according to claim 6, wherein the ischemic disease is myocardial infarction.

10. The method according to claim 6, wherein the ischemic disease is angina pectoris.

11. The method according to claim 6, wherein the ischemic disease is cerebral infarction.

12. The method according to claim 6, wherein the ischemic disease is cerebral hemorrhage.

13. The method according to claim 1, wherein the newly forming tissue is dermal tissue, muscular tissue or connective tissue.

14. The method according to claim 13, wherein the newly forming tissue is dermal tissue.

15. The method according to claim 13, wherein the newly forming tissue is muscular tissue.

16. The method according to claim 13, wherein the newly forming tissue is connective tissue.

* * * * *